(12) United States Patent
Kissinger

(10) Patent No.: US 8,052,617 B2
(45) Date of Patent: Nov. 8, 2011

(54) PORTABLE SAMPLING OR TESTING DEVICE AND METHOD FOR PHARMACOKINETICS AND PHYSIOLOGY STUDIES

(75) Inventor: Candice B. Kissinger, West Lafayette, IN (US)

(73) Assignee: Phlebotics, inc., West Lafayette, IN (US)

( * ) Notice: Subject to any disclaimer, the term of this patent is extended or adjusted under 35 U.S.C. 154(b) by 1339 days.

(21) Appl. No.: 10/914,733

(22) Filed: Aug. 9, 2004

(65) Prior Publication Data

US 2006/0102091 A1 May 18, 2006

(51) Int. Cl.
*B65D 81/00* (2006.01)

(52) U.S. Cl. .................. 600/573; 600/578; 600/579

(58) Field of Classification Search .............. 600/579, 600/573, 575, 576, 578; 119/421; 604/317, 604/327, 151
See application file for complete search history.

(56) References Cited

U.S. PATENT DOCUMENTS

| | | | |
|---|---|---|---|
| 1,482,955 A * | 2/1924 | Tideman | 16/19 |
| 4,077,395 A * | 3/1978 | Woolner | 600/575 |
| 4,696,309 A * | 9/1987 | Stephan | 600/575 |
| 4,832,294 A | 5/1989 | Eidem | |
| 5,423,738 A | 6/1995 | Robinson et al. | |
| 5,556,065 A | 9/1996 | Wadley | |
| 6,062,224 A * | 5/2000 | Kissinger et al. | 128/897 |
| 6,183,442 B1 | 2/2001 | Athanasiou et al. | |
| 6,390,311 B1 | 5/2002 | Belokin | |
| 6,547,755 B1 | 4/2003 | Lippe et al. | |
| 6,736,783 B2 * | 5/2004 | Blake et al. | 600/582 |
| 2002/0091454 A1 * | 7/2002 | Vasko | 700/65 |
| 2006/0009727 A1 * | 1/2006 | O'Mahony et al. | 604/4.01 |

OTHER PUBLICATIONS

International Searching Authority, International Search Report, Aug. 12, 2008.
International Searching Authority, Written Opinion of the International Searching Authority, Aug. 12, 2008.

* cited by examiner

*Primary Examiner* — Kevin C Sirmons
*Assistant Examiner* — Laura Schell
(74) *Attorney, Agent, or Firm* — Baker & Daniels LLP

(57) ABSTRACT

A portable sampling or testing device for pharmacokinetics and physiology studies and a method for using the device in conducting tests on stationary or moving animals, or human test subjects, is disclosed. The device includes an apparatus for conducting a test on a freely moving subject, or a device which may be moved by a technician to be positioned over an immobile subject, such as a premature infant or unconscious human subject in an intensive care ward. The device is designed and sized to be mobile. In one embodiment, the device comprises a wheeled cart which may be moved by a human test subject operably connected to it. In another embodiment, the device comprises a wheeled carriage positioned above an animal which wears a sling connected to the device. The device may include an uninterruptible power supply. The method provides for sampling bodily fluids or acquiring physiological readings from the test subject. The method provides for removal of body fluids with or without reintroduction of the withdrawn bodily fluids back into the freely moving subject.

18 Claims, 10 Drawing Sheets

PORTABLE SAMPLING OR TESTING DEVICE AND METHOD FOR PHARMACOKINETICS AND PHYSIOLOGY STUDIES

BACKGROUND OF THE INVENTION

This invention relates to a device for use in biomedical research, and, in particular, to a system for conducting tests and monitoring conscious and freely-moving animals.

Working with living animals is a requirement for important biomedical research techniques, such as infusion, in vivo microdialysis, in vivo ultrafiltration, in vivo electrochemistry, and electrocardiology. All of these techniques study the performance of living organs, such as the brain, heart, circulatory system, muscles, etc. These techniques also require connections between one or more external devices and one or more sensors or implants in the animal's body. Examples of devices include syringe pumps, fraction collectors, electrometers, vacuum sources, light sources, and potentiostats. Examples of implants include infusion cannulae, ultrafiltration probes, microdialysis probes, and electrodes.

U.S. Pat. No. 6,062,224 discloses an apparatus and a method for conducting automated blood sampling (ABS), the teachings of which are incorporated herein by reference. The method disclosed in that patent includes the step of returning unused blood, that was withdrawn from the test subject and was still remaining in the catheter and associated tubing after collection, back into the animal. The injection of unused blood back into a test subject is important when the subject is a small animal, because in that instance one must be concerned with the conservation of red blood cells (erythrocytes) in the small animal. Red blood cell replenishment requires a period of 10 to 14 days in rodents, therefore a study running over a period of only 1 to 4 days is not long enough for the body to replace any blood cells removed during automated sampling. If too many red blood cells are removed, the animal is at risk of anemia and its associated complications. The return of withdrawn blood into some larger animals, such as humans, may also be needed to conserve erythrocytes if the animal is sufficiently small (e.g., human infants), but in other cases may not be desirable since returned blood would be accompanied by anti-coagulants to keep the blood from clotting while in the automated blood sampling device. Although the required concentration of an anticoagulant, such as heparin, when used in blood return, is less than 2% of the typical therapeutic dose, it may be desirable to seek an alternative approach to automated blood sampling which either does not re-inject blood into the animal being monitored, or returns blood using an alternative means of preventing coagulation of the blood while it is out of the body during connection to the automated blood sampler.

As discussed in U.S. Pat. No. 6,062,224, it is sometimes desirable to monitor the animal while it is active and/or to allow the animal to engage in various types of activity during the testing or monitoring of the animal. For example, rotational and vertical behavior in laboratory rodents is a well-established indicator of neurochemical changes occurring in the animal during testing. The clockwise or counterclockwise preference of the animal, the frequency of such rotation, and similar information concerning the vertical movement of the animal are valuable data. Accordingly, U.S. Pat. No. 6,062,224 and U.S. Pat. No. 5,816,256 disclose movement-responsive systems that include a container for housing the animal and a mechanism for rotating the container in response to rotational movement of the animal.

The devices disclosed in the above-referenced patents are very useful in monitoring small animals because these devices allow for monitoring the animal without undue interference with the movement or normal activities of the animal, and the automation eliminates the need for human handling and the stress associated with such handling. Although this same concept can be envisioned for some larger mammals (e.g. pigs), it would not be practical for all human studies. The exception would be studies in neonatal intensive care units where premature infants are not much different in weight than an average guinea pig, have similar sized veins, and are much less mobile. In the case of neonatal intensive care, a traditional incubator would be substituted for a cage, and automated blood sampling would be conducted under continuous supervision by medical personnel. The advantage of automated blood sampling in premature infants would to be alleviate the trauma associated with multiple "sticks" (insertion of a needle into a vein or artery) during the repeated blood sampling that is necessary to monitor disposition of drug treatments. These patients are highly medicated and because they have undeveloped organs for drug metabolism and excretion, the therapeutic concentration of the drugs used is highly variable. Neonates must be constantly monitored to avoid toxic reactions due to overdose. In these patients, the extremely tiny blood vessels make the process of blood sampling extremely difficult for the phlebotomist (blood sampling technician), traumatic for the patient, and emotionally challenging for the parents and all associated medical personnel.

In human studies that involve the collection of blood for Phase 1 Clinical Trials, there are several other reasons that would justify the use of automated blood sampling, and specifically a mobile device for conducting this process. For example, mobility would be useful to allow a human subject to utilize a private restroom facility without interrupting a test or monitoring session. Humans are more likely to participate in automated blood sampling studies if their movements are unrestricted, and they can move to different rooms within the clinic to eat, watch television, or engage in entertainment like card playing or board games. Automated blood sampling, as well as the automation of other tests conducted during Phase 1 Clinical Trials (such as electrocardiography, blood pressure recording, and body temperature monitoring) can potentially be done with greater temporal accuracy (i.e. the collection of samples at a specific time), and the use of less human personnel, than manual methods of acquiring the same samples and data.

Large animals, such as dogs or pigs, may not respond well to the tethering and movement-responsive caging required for operation of the 6,062,224 and 5,816,256 device. Furthermore, that device may be incompatible with an animal that is agile (monkeys, primates), or able to jump high (monkeys, dogs, rabbits). The movement-responsive cage for a strong animal (pig, horse, sheep, cow, goat) would have to be constructed of even stronger materials, increasing the cost and weight of the device. Tethering would necessarily restrict the animal's movement to the confines of the test cage and may induce test-related stress for the animal. Stress involves release of various hormones, and such hormones have a profound effect on the redirection of blood flow as well as the function of many physiological systems in the body. Therefore, the test conditions should be designed to reduce this stress effect as much as possible. It is therefore desirable to provide a system which does not unduly restrict movement of the animal, does not induce significant test related stress, is reasonable in size, can be manufactured, operated and maintained at reasonable cost, and which is adapted for larger animals including, but not limited to, pigs, cows, horses, dogs, primates, and humans.

SUMMARY OF THE INVENTION

The present invention comprises a portable device for performing at least one biomedical test on a freely-moving animal, including humans. As used herein, "test" may comprise collection of a fluid sample, as in automated blood sampling, sampling of another body fluid, or acquisition of an electronic signal, such as during blood pressure or electrocardiogram monitoring. Equipment to be used in conducting the test, which may include an apparatus for drawing blood and/or for injecting a substance into an animal, for example, is mounted onto a device, such as a carriage, which can be easily moved by the animal, a human technician, or a human subject. Alternatively, the device can be mounted to the animal itself by using, for example, a saddle bag or backpack. The equipment may be powered from a fixed energy source and/or from a self-contained mobile energy source.

According to one embodiment, an ABS apparatus is connected to a freely-moving animal by resiliently compressible tubing. The tubing is operably connected to a refrigerated fraction collector having sealed vials for receipt of blood samples. The tubing is also operably connected to a syringe pump and a source of sterile fluid, such as saline (0.9% sodium chloride solution). The apparatus further includes valves operatively connected to the resilient tubing. The apparatus also includes a sample collection control means, such as a personal computer (PC), a microcontroller, a computer chip with embedded software code, an electronic controller, a timer, or other regulating device.

The tubing of the present invention provides fluid communication between the test animal, the refrigerated fraction collector, and the syringe pump through a three-way connector such as a "Y" or "T" connector. The valves are located so as to control fluid flow to and from these three areas. The valves associated with the tubing which connects the test animal and the refrigerated fraction collector may comprise pinch valves and may be combined within a common housing and utilize individual or common pinch bars. In this manner, the system employs a pinch valve that operates such that whenever one selected tube is open, another is shut. In this embodiment, the test lead, tubing, and "T" connector all have anticoagulant properties, either inherent in the non-thrombogenic (i.e. material not likely to induce blood clotting) plastic used in their construction, or via a permanent or renewable anticoagulant coating in the interior thereof. Because all surfaces in contact with the blood sample in this embodiment are non-thrombogenic, it is possible to use saline solutions, without added heparin or other anticoagulant additives, to flush the system and to move blood samples within the apparatus.

In some cases, it may still be necessary or desirable to use an added anticoagulant as part of the biomedical test. In such case, the added anticoagulant would form a renewable non-thrombogenic film on the interior surface of all tubing and other connections through which it was flushed. Therefore, this system should be able to function either with, or without, anticoagulants such as heparin, sodium citrate or other materials added to the saline used to move blood in and out of the automated blood sampler.

In one embodiment, the control means (controller) coordinates the valve positions, fraction collector, and syringe activity so as to flush the system, withdraw a blood sample from the animal, move that blood sample to the refrigerated fraction collector, and advance the fraction collector to the next vial position or to waste. The controller can also regulate the refilling of the syringe pump with sterile saline solution from a sterile saline solution supply means. Because the controller is easily programmed with various test protocols, the controller can be programmed such that no blood is re-injected into the test subject. In that case, blood would be continuously sampled in small volumes on the order of microliters, at intervals spanning as short a time as possible (less than 3 minutes). If desired, blood which is withdrawn during a particular cycle and not used as a sample may be flushed out of the apparatus and associated catheter during an ensuing cycle.

In one embodiment, the ABS apparatus, the controller, and an uninterruptible power supply are situated on a carriage of a size that allows the freely-moving animal, a mobile human subject, or a human technician to easily move the entire device. Accordingly, the freely-moving animal is not overly restricted in its activities. The animal may be allowed to roam within a larger area such as a room, or containment area, and perform normal functions such as eating, sleeping, and/or elimination without affecting the biomedical test. In the case of a human test subject, the human may recline in a bed, lounge in a chair, walk down a hallway, and use a wheelchair-compatible toilet stall without interfering with the biomedical test. Such a device may be less stressful than systems or protocols which restrain movement.

DETAILED DESCRIPTION OF THE INVENTION

Figure 1:
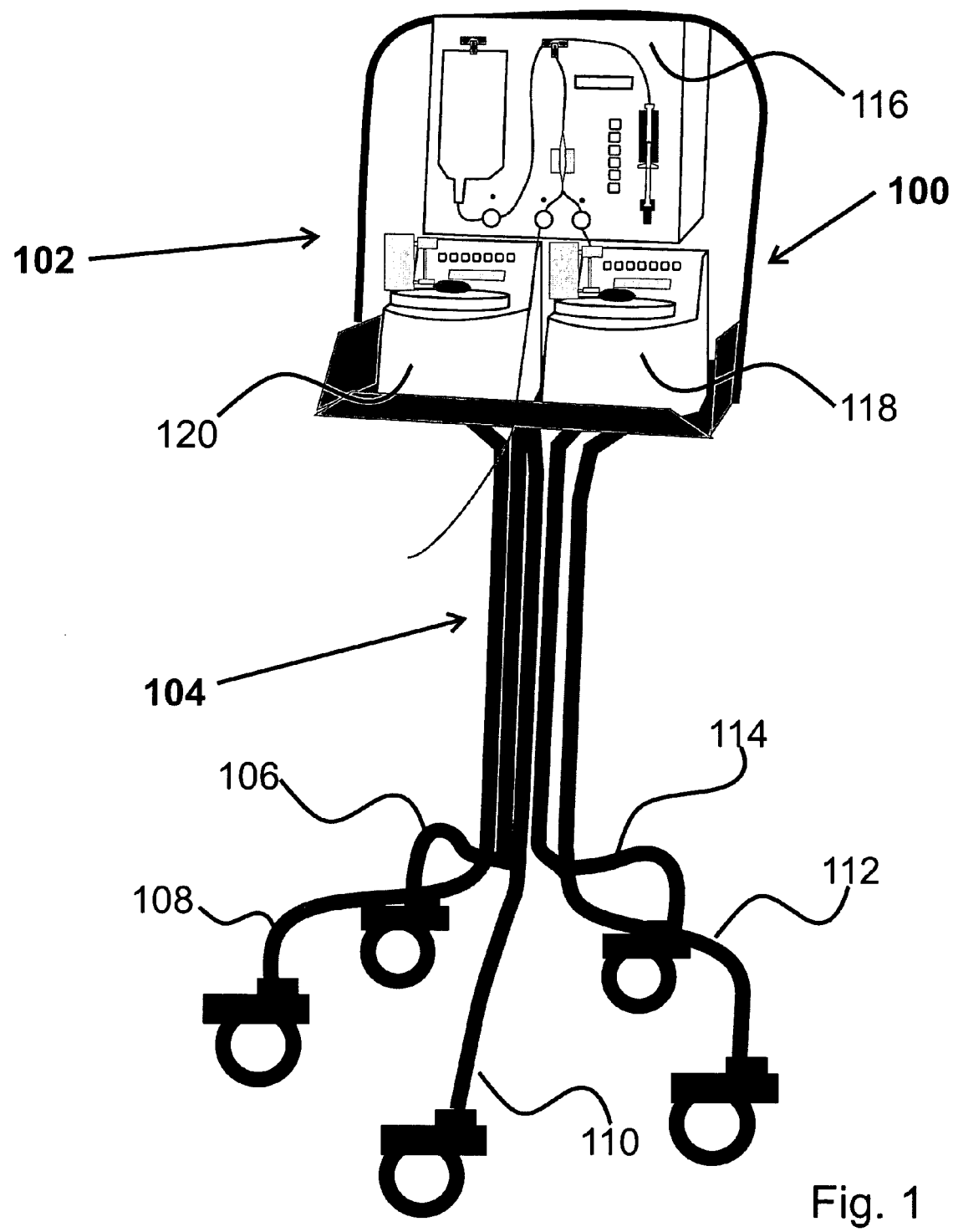
FIG. 1 shows a perspective front view of one embodiment of the apparatus of the present invention that might be used for large animals or human subjects.
Figure 1A:
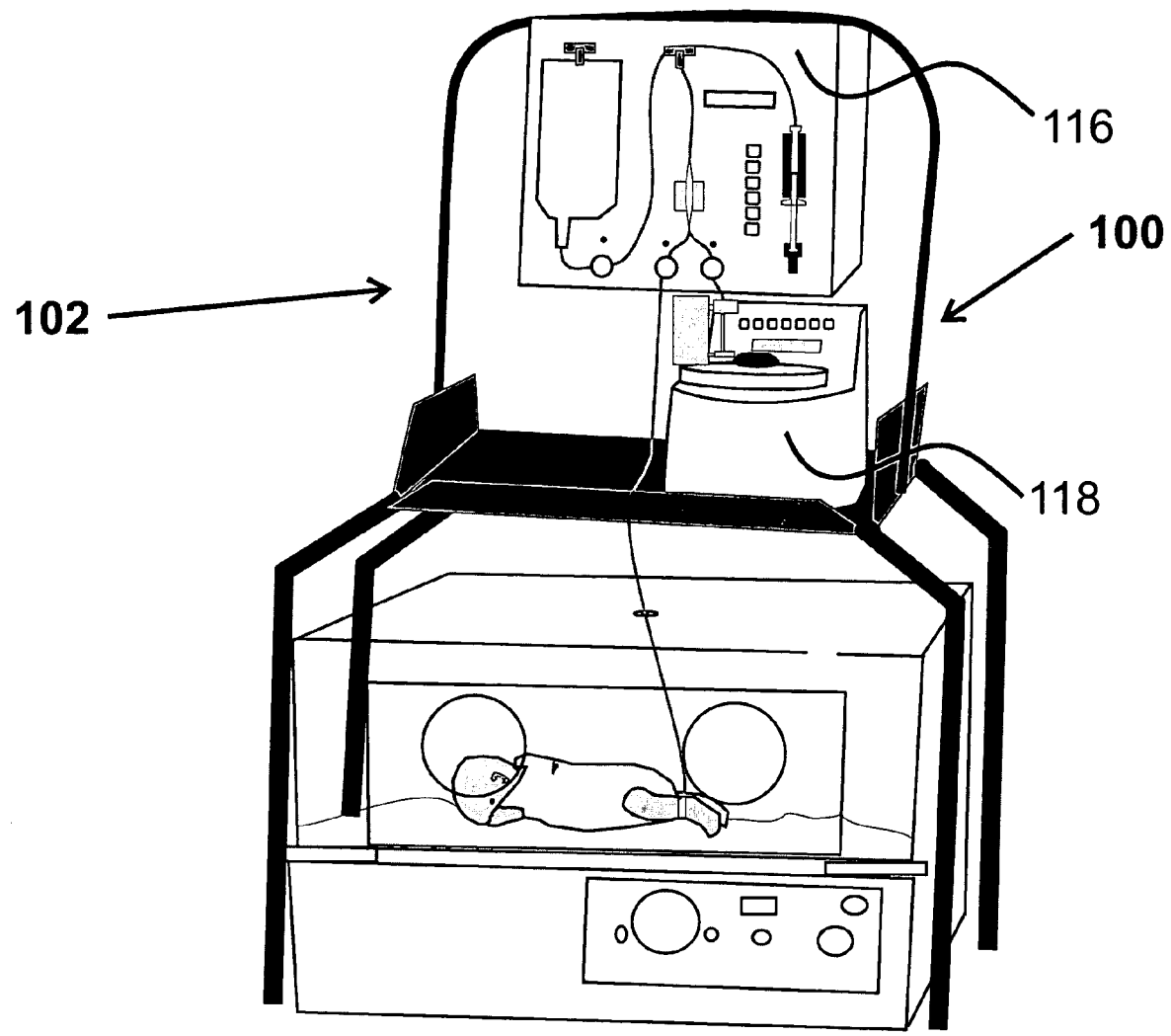
FIG. 1A shows an embodiment of the apparatus in FIG. 1 modified for use above an incubator used in a neonatal intensive care environment

Referring now to FIG. 1, there is shown a perspective front view of one embodiment of the apparatus of the present invention. Specifically, in this embodiment, portable device 100 is capable of being moved by a test subject, such as a human, or by a laboratory assistant when the test subject is a different type of large animal. In this embodiment, portable device 100 comprises equipment section 102 and mobile base 104. Mobile base 104, in this embodiment, includes legs 106, 108, 110, 112 and 114, each of which have a wheel attached thereto to permit base 104 to be wheeled about in any direction. The number of legs, and the height and shape of the legs, is a design choice, and are all contemplated to be within the scope of the invention. The use of wheels, roller balls, or other means to allow free movement of this device is likewise a design choice, and are all contemplated to be within the scope of the invention. For example, it may be desired to provide devices of various heights to accommodate test subjects of various heights. Alternatively, a single unit with a varying height may be designed. All of theses variations are within the scope of the present invention.

Figure 2:
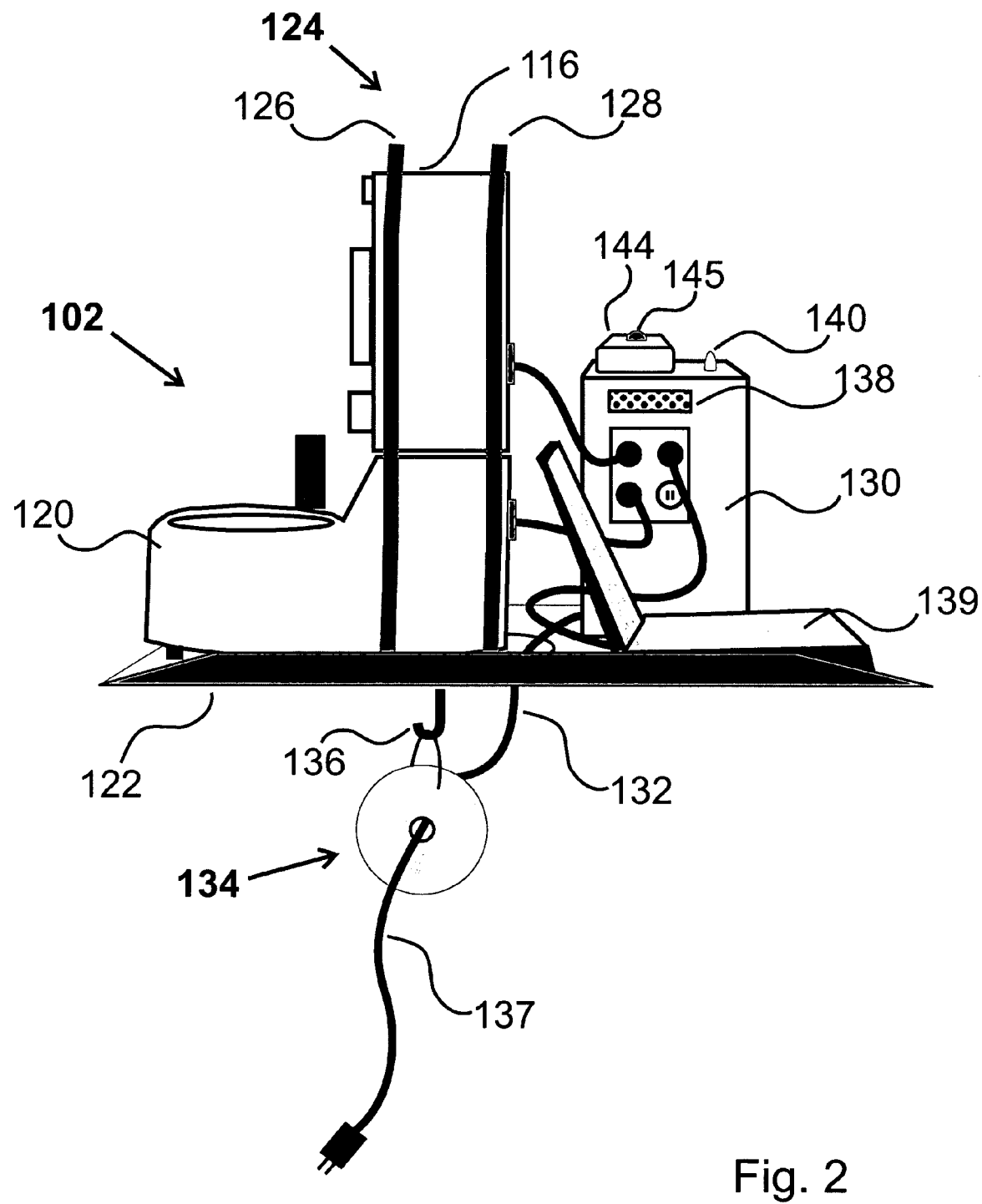
FIG. 2 shows a side view of the tray section of the apparatus of FIG. 1.

Continuing with FIG. 1, equipment section 102 includes an apparatus for performing a biomedical test on the test subject, which, in this embodiment, comprises ABS 116. Also shown in FIG. 1 are refrigerated fraction collectors 118 and 120. Referring now to FIG. 2, a partial side view of the device of FIG. 1 is shown, showing additional detail of equipment section 102. Equipment section 102 comprises lower support 122 and bracket support 124 which comprises bracket 126 and bracket 128. Bracket support 124 is used in this embodiment to mount ABS 116 above refrigerated fraction collector 120. Refrigerated fraction collector 120 is supported by lower support 122.

Also shown in FIG. 2 is portable power supply 130, which in this embodiment comprises an uninterruptible power supply (UPS) and a microprocessor. Power for portable supply 130 is typically provided through cord 132 and extension cord unit 134 hanging from hook 136. Extension cord 137 of extension cord unit 134 is connected to a power source such as a wall socket. Control means 130 also comprises speaker 138 and warning light 140. When no power is sensed from cord 132, control means 130 causes an intermittent audible alarm to be sounded through speaker 138 to ensure those in the vicinity are aware that external power is not being supplied. In this embodiment, alarm light 140 flashes one color (e.g. yellow) when external power is not being supplied, and flashes another color (e.g. red) when the internal battery in the portable power supply reaches a predetermined discharge level. While the main power is disconnected, such as by removal of cord 137 from the wall socket, power to all units plugged into the power supply is maintained by its internal battery. Units plugged into control means 130 in FIG. 2 include ABS 116, collector 120, laptop computer 139, but could include additional devices being transported by the portable pharmacokinetic and physiologic sampling and monitoring system.

Continuing with FIG. 2, control means 130 may also incorporate location monitor 144, which could also be placed on bracket 126, bracket 128, lower support 122, ABS 116, fraction collector 120, or other places on the system. Location monitor 144 comprises a transponder and/or transceiver that is used to find the location of a mobile unit within a research facility. A unique code associated with each cart is transmitted to a receiving unit mounted in the ceiling, wall, door or floor of each room in the facility. This code is then displayed on a view screen at a central monitoring station receiving information from each individual receiving station, enabling technicians to locate a specific cart within the confines of the research facility. An optional panic button 145 can be activated by the patient or a technician to alert personnel at the central monitoring station of an emergency situation. FIG. 2 also shows computer 139, which is used to upload information about the blood sampling protocol to a controlling computer chip located inside ABS 116, and to receive downloads from that chip confirming all sampling steps and operations of ABS 116 and fraction collector 120. In the embodiment in FIG. 1 and 2, computer 139 is a laptop computer also receiving power from power supply 130. It is also envisioned that such a computer could be located in a central station with uploads and downloads communicated to the portable device via a choice of mechanisms, examples of which include (a) a portable flash card which transfers to a USB or other hardwired connection port on the computer and also on the ABS 116 unit (b) a wireless network transmission of data to and from the central computer (c) a temporary connection of a cable between the ABS 116 unit and the external computer or (d) an infrared transmission between the computer and the ABS 116 unit or (e) other common means of communication between a computer and a peripheral device.

The selection of the means for support is a design choice, and fewer or more supports of the same or differing form may be used, and all are contemplated to be within the scope of the invention. Supports or combinations of supports may include additional brackets, shelves, trays, hooks, drawers, rods, hangers and others. The combination of bracket support 124 and lower support 122 provides the ability to mount equipment in a variety of horizontal and vertical relationships. Moreover, incorporation of additional equipment is facilitated. By way of example, but not of limitation, a transceiver may be attached or supported by either bracket support 124 or lower support 122 to allow for wireless transmission of data from portable device 100 to a remote device, such as a computer, in the event test control means 130 does not include a transceiver or in the event additional bandwidth is desired. The data transmitted may comprise test data and/or data from a global positioning receiver or other tracking device. Similarly, in the event physiological monitoring is desired, the requisite equipment for such monitoring may be easily incorporated into portable device 100.

Figure 3:
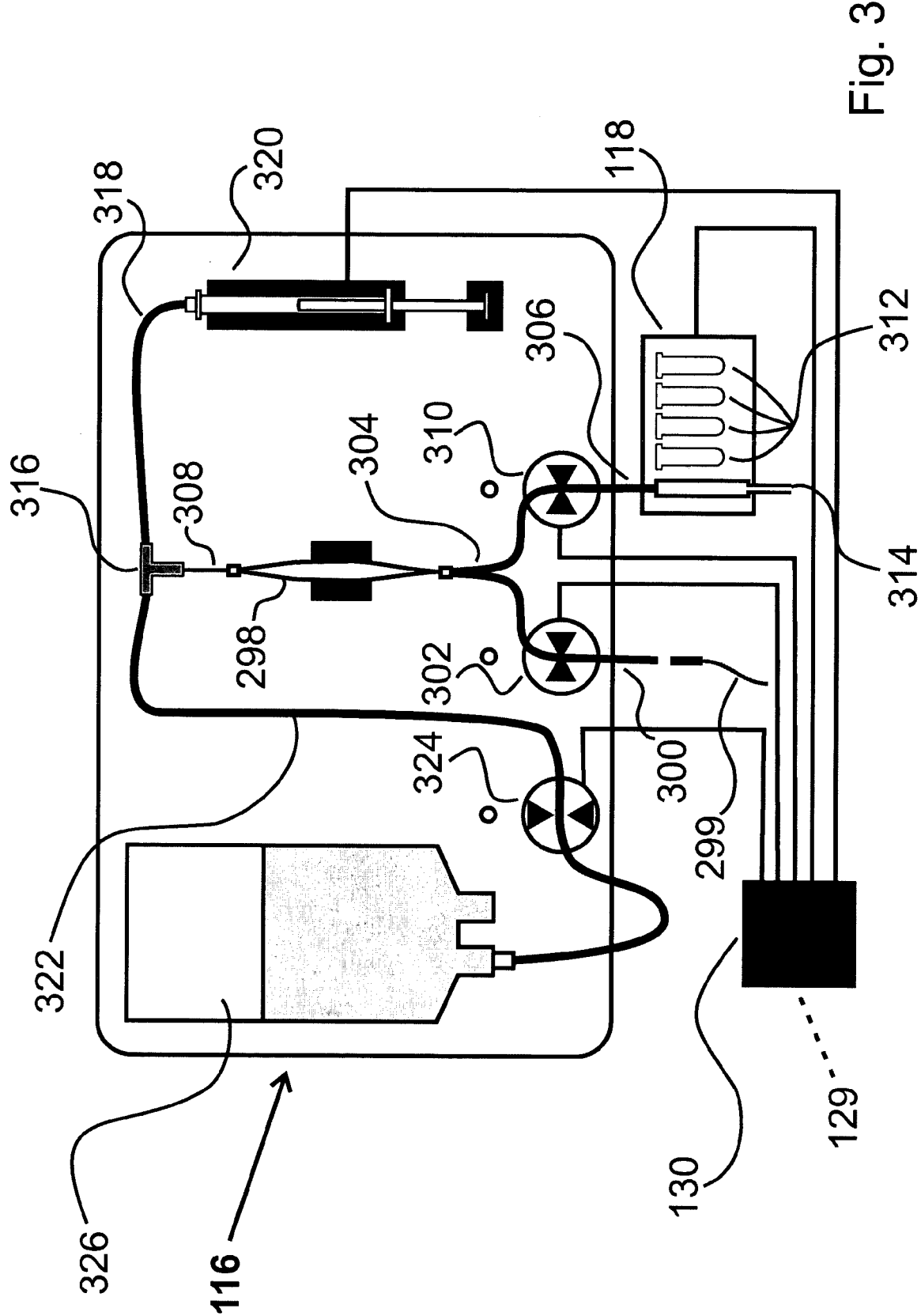
FIG. 3 shows a diagrammatic view of one embodiment of an apparatus for automated sampling of blood.

FIG. 3 shows a diagrammatic view of ABS 116. In this embodiment, one end of catheter tubing 300 is operably connected to test lead 299 which is a catheter which has its distal end inserted into a vein or artery in the test subject using devices and methods well-known in the art. Catheter tubing 300 is routed through first pinch valve 302 to first intersection or "T" 304, where catheter tubing 300 is joined with collector tubing 306 and reservoir tubing 308. Collector tubing 306 extends from first "T" 304 through second pinch valve 310 to refrigerated fraction collector 118. Fraction collector 118 includes sealed vials 312 for receiving blood samples, and also includes drain 314, all as is well known in the art. The present invention includes within its scope use of sample collection means other than refrigerated fraction collectors. For example, it will be appreciated by those skilled in the art that for performance of some experiments, the sample collection means will not require a drain, and the saline and sample may be intentionally intermixed.

Connector tubing 308 extends from first "T" 304 and reservoir 298 to second intersection or "T" 316. It will be appreciated by those skilled in the art that reservoir 298 can alternatively be an extension of tubing 308 or the enlarged section of tubing as depicted for reservoir 298 in FIG. 3. Extending from second "T" 316 is syringe tubing 318 which is, in turn, connected to syringe pump 320. Syringe pump 320 is of the type that can be controlled to move fluid to or from syringe tubing 318, and may comprise, for example, the Culex ABS syringe drive manufactured by Bioanalytical Systems, Inc. of West Lafayette, Ind. It will be appreciated by those skilled in the art that other means for moving fluid can be substituted for syringe pump 320 and are considered within the scope of this invention. Other means for moving fluid include, but are not limited to, a reciprocal piston pump, peristaltic pump, or any other vacuum/pressure source.

Reservoir tubing 322 extends from second "T" 316, goes through third pinch valve 324 and is connected to sterile saline reservoir 326. Sterile saline or any other physiologically compatible solution, such as Ringer's solution, may be housed within saline reservoir 326. First, second and third pinch valves 302, 310 and 324, respectively, in the embodiment of FIG. 3, are intended for use with only a single tube—to open or close that tube—and may comprise, for example, Model 161P, manufactured by NR Research of Caldwell, New Jersey. It is also anticipated that with a double pinch valve, such as that used in the Empis Automated Dosing device, manufactured by Bioanalytical Systems Inc., West Lafayette, Indiana, could be used in situations where two different blood vessels are alternately being sampled. In that example, a second syringe drive, tubing set and saline reservoir would mount to the front panel of ABS 116. The fraction collector 118, such as the HoneyComb model manufactured by Bioanalytical Systems Inc., West Lafayette, Indiana, would possess dual sampling needles so that only one collector would be required.

It will be appreciated by those skilled in the art that a wide variety of fluid control means can be used in place of first pinch valve 302, second pinch valve 310 and third pinch valve 324. For example, first pinch valve 302 and second pinch valve 310 may be replaced with a single three-way pinch valve, alternatively, in-line valves may be used. It will be further appreciated by those skilled in the art that it is not necessary to have sterile saline reservoir 326 in the apparatus for performing automated micro blood sampling. For example, in another embodiment, syringe pump 320 is connected to syringe tubing 318 which is in turn connected to first "T" 304. In this other embodiment, second "T" 316, connector tubing 308, and third pinch valve 324 are omitted.

The blood sampling system of FIG. 3 also includes controller 130 for automated control of the system as is described in greater detail herein. Controller 130, which comprises, in this embodiment, a computer chip with embedded software code, is operatively connected, by means well-known in the art to: (a) first pinch valve 302; (b) second pinch valve 310; (c) third pinch valve 324; (d) syringe pump 320; and (e) fraction collector 118. In addition, there must be a transfer of information to controller 130 chip from user interface software located in an external computer 129 which uploads user preferences to controller 130 by means of (a) a cable (b) a flash card (c) a wireless network connection (d) a Bluetooth connection, or any another established method of communication between the external computer and peripheral devices. By its operable connections, controller 130 controls the positions of first pinch valve 302 and second pinch valve 310 to cause the alternate opening and closing of test lead 300 and collector tubing 306; controls the open and closed position of third pinch valve 324, to cause the opening and closing of reservoir tubing 322; controls syringe pump 320 for delivering fluid into or withdrawing fluid from syringe tubing 318; and instructs fraction collector 118 to either receive blood samples into the vials 312 or to pass fluid coming from collector tubing 306 into drain 314.

The present invention may be used to sample body fluids other than blood, either separately or in combination with blood sampling and other biomedical testing. Cerebrospinal fluid (CSF), for example, may be sampled using the present invention. The combination of CSF and blood sampling allows for a complete picture of the disposition of a drug, metabolite or biomarker on both sides of the blood brain barrier. Other applications will be known to those skilled in the art and are within the scope of the present invention.

Figure 4:
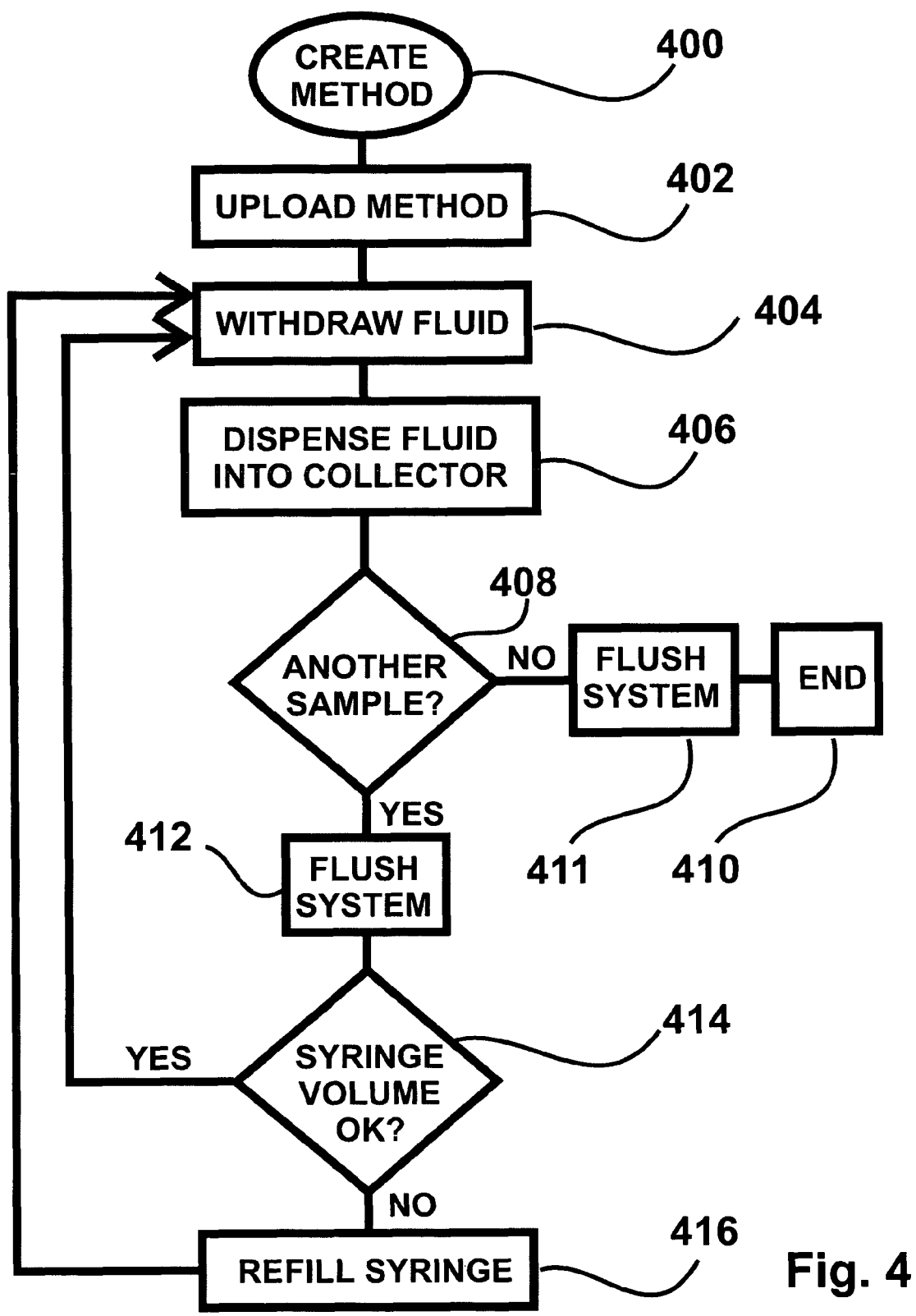
FIG. 4 shows a flowchart of one embodiment of the method of the present invention for conducting automated micro sampling of blood.

Operation of one embodiment of ABS 116 is explained by referring to FIG. 4. FIG. 4 is a flow chart of one method for conducting automated blood sampling according to the present invention. At step 400, the operator outlines the blood sampling method to be used in the study, using the user interface software on a computer. This method includes, among other information, the time of the sample, the volume of the sample and whether or not the sample will be diluted with saline. These decisions are translated by the computer software into a series of instructions which are then uploaded to the automated blood sampler in step 402. During step 402, automated internal system checks would verify the correct operation of the fraction collector (FIG. 1, 118 or 120) and controller (FIG. 1, 116) prior to accepting the upload of the method defined by the user in step 400.

Prior to step 400, the tubing and syringe pump would already be loaded and flushed with saline. The catheter in the test subject would be connected to ABS 116 only after this flushing procedure was complete. This process is described in detail in the next paragraphs. Catheter tubing 300, collector tubing 306, reservoir 298, connector tubing 308, syringe tubing 318, and saline tubing 322 are all filled with sterile saline solution residing in saline bag 326 according to the following steps:

(a) Pinch valve 302 and pinch valve 310 are placed in the closed position and pinch valve 324 is placed in the open position.
(b) Syringe pump 320 is operated to withdraw a predetermined amount of saline from saline reservoir 326. The predetermined amount is determined by the maximal volume of the syringe on syringe pump 320. One or more refills of the syringe may be required to accomplish complete flushing of all tubing. The required volume must be at least as great as the total volume of catheter 299, catheter tubing 300, twice the volume of collector tubing 306, reservoir 298, connector tubing 308, syringe tubing 318, and reservoir tubing 322, plus the volume of first and second "T"s 304 and 316, respectively, if first and second "T"s 304 and 316 introduce additional volume as would be the case if first and second "T"s comprise separate connectors, and the volume of any desired flush (as described at step 412 below).
(c) Pinch valve 324 is then closed.
(d) Pinch valve 302, or pinch valve 310, is then opened and Syringe pump 320 is instructed to deliver saline until syringe pump 320 is empty. During this delivery of saline, reservoir 298, tubing 304 and tubing 308 are all inverted so that as the fluid enters reservoir 298, any associated air bubbles will rise with the fluid front and be pushed out more easily into fraction collector 306 tubing. If this procedure is not followed, air bubbles will rise towards "T" 316 and be harder to expel from the system. If there was insufficient fluid in the line to accomplish the purge of all air and air bubbles from the system, then pinch valve 324 is opened again, pinch valve 302 and 310 are closed again, and the plunger of the syringe on syringe pump 320 is retracted again to refill the syringe. Valve 324 is then closed, valve 302 remains closed, and valve 310 is opened again. Step (d) is then repeated until tubing 318, 308, 322 and 306 are all filled with saline and free of air and air bubbles.
(e) The syringe is refilled again as described in step(b).
(f) Tubing 304 and 308 are returned to the original position shown in FIG. 3, and valve 310 and 324 are closed, while valve 302 is opened. Then syringe pump 320 is instructed to deliver fluid to catheter tubing 300 through opened valve 302 until all air is expelled from tubing 300.

(g) A connection can now be made between catheter tubing 300 and catheter 299. Valve 302 will then be opened, while valves 310 and 324 remain closed. Syringe pump 320 is instructed to withdraw fluid from tubing 318 and thus withdraw fluid from all fluid lines connected to tubing 318, including tubing 308, 304, 300 and catheter 299. This action draws blood into each successive tubing until the syringe pump is instructed to stop. Typically, this process will draw only enough blood to capture any air bubble which may have been formed during connection of catheter 299 to catheter tubing 300. Once the air bubble passes into "T" 304 or enters reservoir 298, valve 302 is closed. Then valve 310 is opened and syringe pump 320 is instructed to deliver fluid to line 318, "T" 316, tubing 308, reservoir 298, "T" 304, and fraction collector tubing 306 in order to flush the air bubble, and all blood in these connections, to the drain on the fraction collector.

(h) Valve 310 and 324 are then closed, and valve 302 is opened. The syringe pump continues to deliver fluid to line 318 and thus flushes blood in the catheter tubing and catheter back to the test subject.

(i) At any time in this process, if there is insufficient fluid in the syringe, the system can be refilled according to the method outlined in step (e).

(j) At any time in this process, if there is too much fluid in the syringe, thereby preventing syringe plunger 320 from being retracted because the syringe is already full, the system can purge excess fluid by opening only valve 310 and expelling the extra fluid.

Returning to FIG. 4, in step 404 blood is withdrawn from the test subject of an amount sufficient to produce a blood sample. To withdraw blood, first pinch valve 302 (FIG. 3) must be opened and pinch valves 310 and 324 must be closed. Then, syringe pump 320 is controlled to withdraw saline of a volume equal to the volume of catheter 299, catheter tubing 300 and first "T" 304 plus an amount equal to the volume of the desired blood sample. This results in catheter 299, catheter tubing 300, first "T" 304 and some or all of reservoir 298 being filled with blood.

To place the withdrawn blood sample volume into fraction collector 118, indicated as step 406 (FIG. 4), the following steps are then taken:

(a) First pinch valve 302 and 324 are closed and pinch valve 310 is opened.

(b) Fraction collector 118 is controlled so that fluid goes to drain 314.

(c) Syringe pump 320 is instructed to deliver saline of a volume at least equal to the volume of collector tubing 306 and the remaining volume of first "T" 304 that is not yet filled with blood from step 404. This step moves blood into collector tubing 306 and to the end of collector tubing 306 nearest fraction collector 118, thus displacing the saline that was previously filling that line (d) Fraction collector 118 is instructed to advance one of the vials 312 so that fluid passes to one of vials 312.

(e) Syringe pump 320 is controlled to introduce saline of a volume equal to the volume of the blood sample, thereby forcing the blood sample into one of vials 312.

Returning to FIG. 4, if, at step 408, it is determined that no additional blood samples are necessary or desired, the method of blood sampling ends at step 410 with the flushing of blood from all tubing and the catheter during step 411. If, on the other hand, additional blood samples are necessary or desired, in step 412 the same flush is performed, fraction collector 118 is realigned over the drain, and syringe pump 320 is refilled in anticipation of the next sample.

At step 414, it is determined, by controller 130, whether syringe pump 320 has a sufficient volume of sterile saline available to perform another blood test. If enough saline is available, the method returns to step 404 to withdraw additional blood. If insufficient saline is available, syringe pump 320 is filled with additional saline at step 416.

The situation described above reflects a situation wherein the unused withdrawn blood or other fluid, remaining in test lead 299 and some of first "T" 304, is returned to the test subject to conserve blood cells and prevent anemia. There may be other examples, in which it is not desirable to do this. For example, when the test subject is a human there may be conditions in which anticoagulant use in the automated blood sampler may be contraindicated by a test subject's use of therapeutic anticoagulants, such as warfarin, due to a preexisting medical need. In such cases, it may be undesirable to re-introduce blood back into the test subject when an anticoagulant is required due to the nature of the tubing being used on the ABS. In these situations, reintroduction is avoided by maintaining pinch valve 302 in the closed position until such time as a sample is to be withdrawn. This means that all blood passing through pinch valve 302 is prevented from returning along the same path by the subsequent closure of pinch valve 302. However, because blood is maintained outside of the body in catheter 299 and catheter tubing 300, care must be taken to rapidly flush blood from the tubing beyond valve 302 and advance to the next withdrawal of blood in order to avoid keep the blood moving in the catheter 299 and catheter tubing 300 and avoid the situation where blood is stationary for prolonged periods of time, since this would increase the potential for blood clotting and obstructing catheter 299 and catheter tubing 300.

According to one embodiment, a near continuous withdrawal is conducted, with each withdrawal taking place over a period measured in seconds, and totaling between 5 and 250 microliters to avoid significant loss of blood from the test subject. According to this method, the time between sampling is minimized. The withdrawal step may be relatively slow to preserve the integrity of the blood cells during their passage through the narrow bore tubing of the catheter 299 and catheter tubing 300, while the intervening steps are conducted somewhat faster through larger bore tubing in fraction collector tubing 306. Thus, blood is not allowed to remain stagnant in test lead 299, or anywhere in the system, for a significant amount of time. This approach is useful in situations wherein a discreet sample at a given time is not needed.

Figure 5:
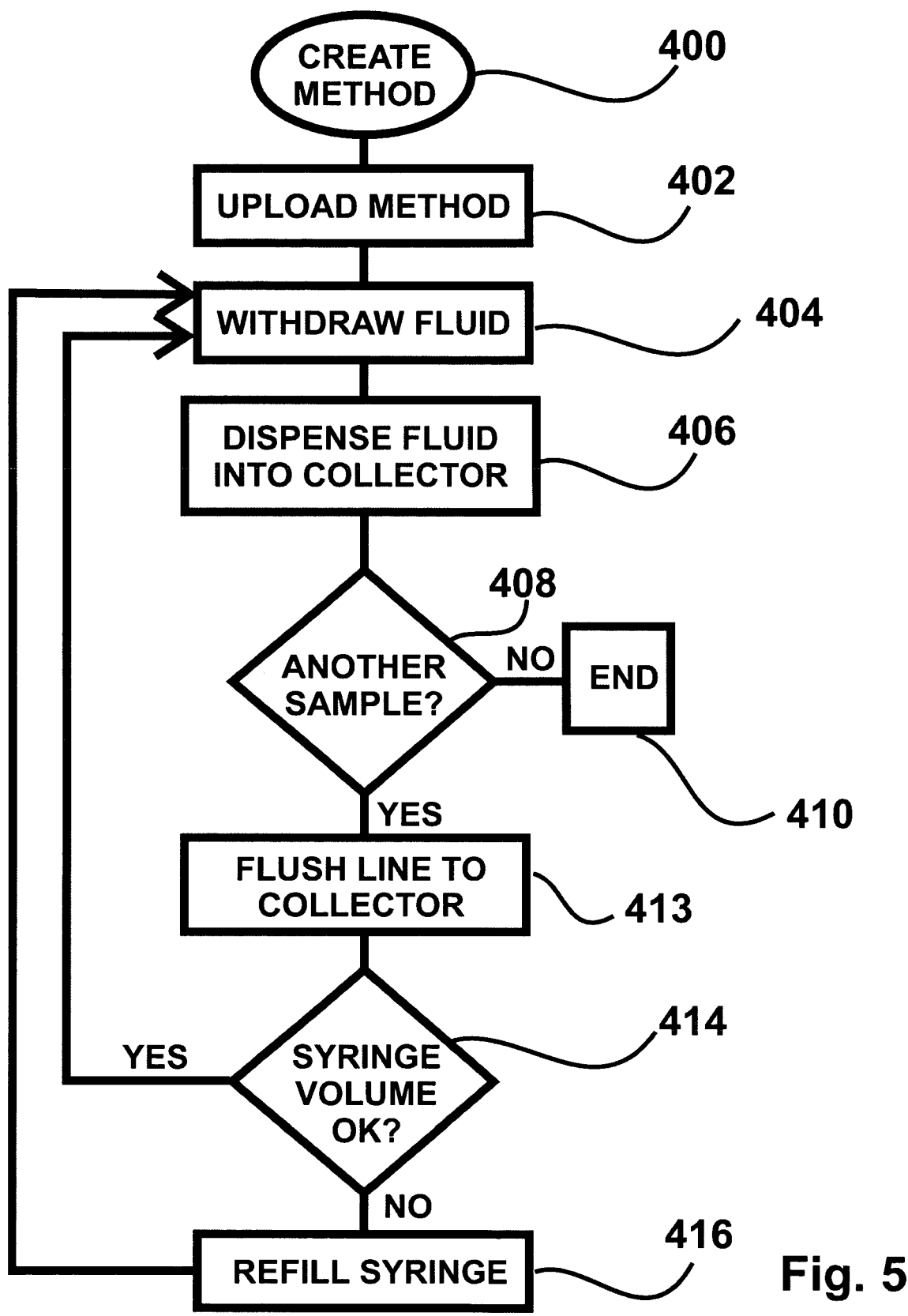
FIG. 5 shows a flowchart of a modification of the method of FIG. 4.

If the time between samples is short enough to avoid blood coagulation in the catheter and catheter tubing, then the process may be modified as shown in FIG. 5. In this procedure, the process of FIG. 4 is modified by removing step 411 and changing step 412 to new step 413. At step 413, the flush is restricted only to tubing 318, "T" 316, tubing 308, reservoir 298, "T" 304, tubing 306 and fraction collector 118. Valve 302 remains closed throughout the flushing step and blood remains in half of "T" 304, catheter tubing 300 and catheter 299. Syringe pump 320 can refill at any time by closing valve 310 and 302, opening valve 324 and retracting the plunger on syringe pump 320 as described previously. After blood has been flushed, valve 302 is opened and the next aliquot of blood is pulled into "T" 304 and reservoir 298. This process continues until such time as the last blood sample is taken. Then, the process ends when the catheter is physically removed from the test subject and the syringe, saline 326 and all tubing on controller 116 are removed and discarded.

It will be appreciated by those of skill in the art that, with the exception of connecting catheter 299 to catheter tubing 300, steps 404-416 may be controlled by controller 130 to result in an automated blood sampling method. Steps 400-402 cover the selection and initiation of the blood sampling method to be automated. A blood sampling method would define (a) when a blood sample was taken, (b) how much blood was taken and (c) whether the blood was to be intentionally diluted with saline, or not. Controller 130 must be able to send control signals to pinch valve 302, pinch valve 310, pinch valve 324, syringe pump 320, and fraction collector 118, all of which are operably connected to controller 130. In one embodiment, controller 130 receives a signal from syringe pump 320 indicative of the saline volume in syringe pump 320 to ensure proper volumes of saline are pumped and withdrawn, and/or are available for obtaining the next blood sample.

Figure 6:
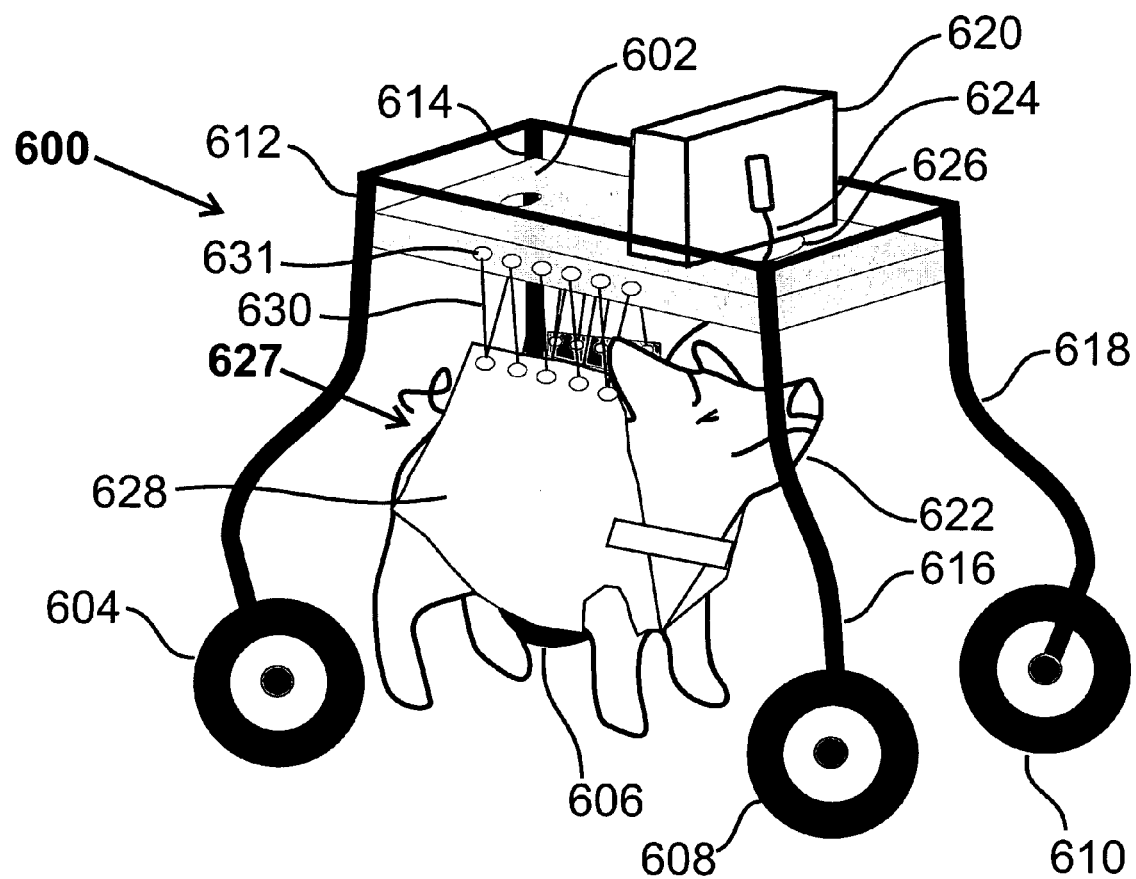
FIG. 6 shows a perspective view of an alternative embodiment of the apparatus of the present invention that might be used for a large animal moving on its own recognizance.

Referring now to FIG. 6, there is shown a perspective view of an alternative embodiment of the present invention, which is intended for use with freely-moving animals In this embodiment, portable sampling or monitoring device 600 comprises base section 602. Wheels 604, 606, 608 and 610 are connected to base 602 by legs 612, 614, 616 and 618 respectively.

Testing or sampling device 620 is positioned above the test subject on base section 602. Thus, base section 602 serves as an equipment section in this embodiment. Testing device 620 is connected to test subject 622 by test lead 624. Test lead 624 passes through hole 626 in base section 602. Keeping test lead 624 within the space defined by portable device 600 protects tube 624 from becoming trampled, twisted, entangled or crushed.

In this embodiment, portable sampling or monitoring device 600 comprises harness 627. Harness 627 includes sling 628 and strap 630. Sling 628 is connected to portable device 600 by passing strap 630 through holes 631 in base section 602.

Figure 7:
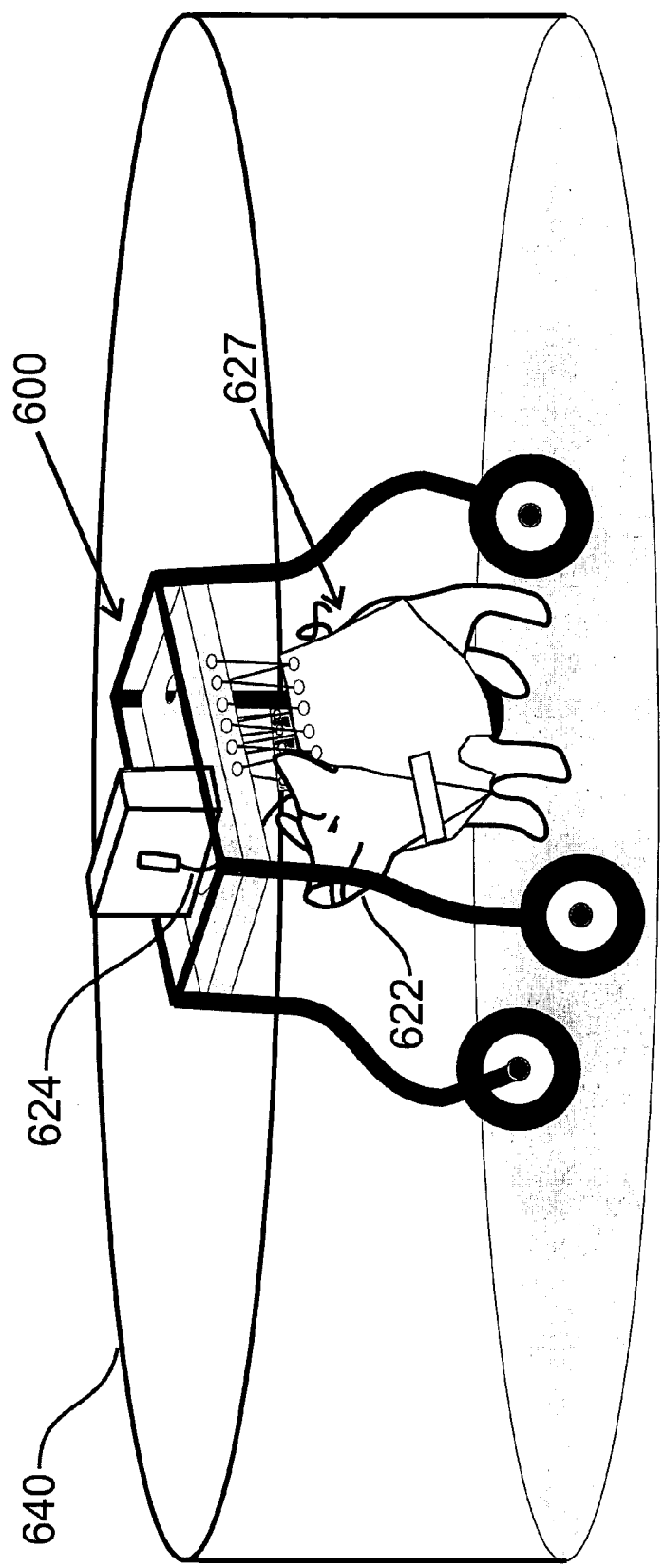
FIG. 7 shows a perspective view of the embodiment of FIG. 6 in use within a containment area.

FIG. 7 shows a perspective view of the embodiment of FIG. 6 in use within a means for constraining the movement of the test subject within a confined area, such as the space below a video monitoring camera. Portable sampling or monitoring device 600 is attached by test lead 624 and harness 627 to test subject 622. Portable sampling or monitoring device 600 and test subject 622 are located within an area defined by an obstruction. In this embodiment, fence 640, defines a containment area. Sampling or monitoring device 600 cannot pass beyond fence 640, thus test subject 622 is maintained within the containment area.

Figure 6A:
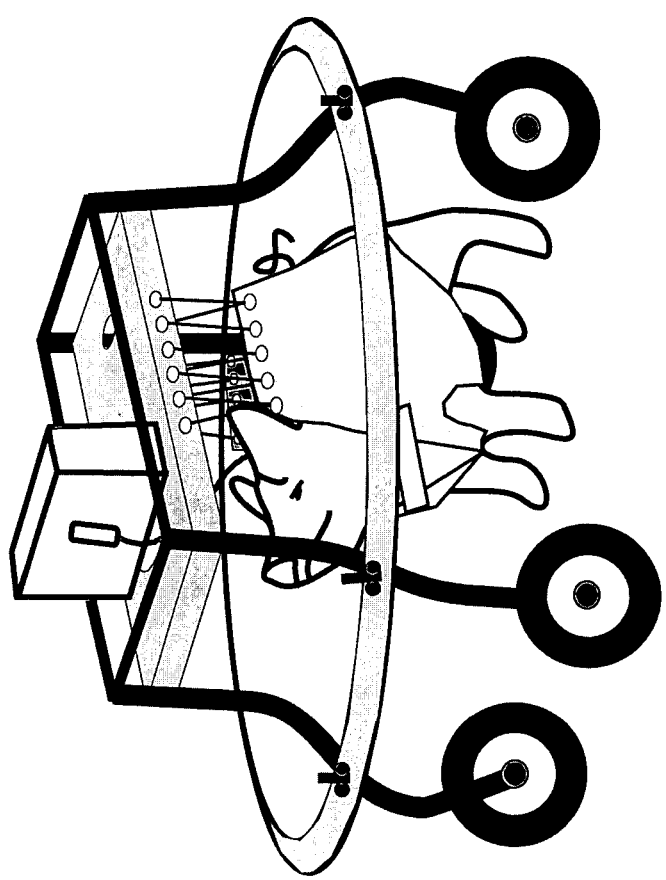
FIG. 6A shows the same apparatus as FIG. 6, but with an added shield which would prevent the apparatus from being wedged in the corner of a square or rectangular cage surrounding a containment area.

As will be appreciated by those of skill in the art, the means for containing the movement of the test subject installed in portable sampling or testing device 600 may also comprise the attachment of a lead, leash, or tether, having one end constrained to an immobile object such as a ceiling. Alternatively, additional shapes of the cage enclosure 640 may be used as a containment area, including such permutations as mazes which would allow the test subject to be trained to navigate the maze, and/or challenged with various maze-related problems while simultaneously being sampled or monitored, and such permutations are contemplated to be within the scope of the invention. However, construction of a containment area should take into account the configuration of the portable device 600. By way of example, but not of limitation, if the portable device 600 is substantially rectangular as shown in FIG. 7, then a containment area of a generally circular shape should be used so as to avoid having a test subject become trapped within a corner of the containment area. Alternatively, the addition of a generally round shield, of a height less than the height of the cage wall, as shown in FIG. 6A, would enable the portable sampling and monitoring device 600 to be used in containment areas of virtually any configuration.

Figure 8:
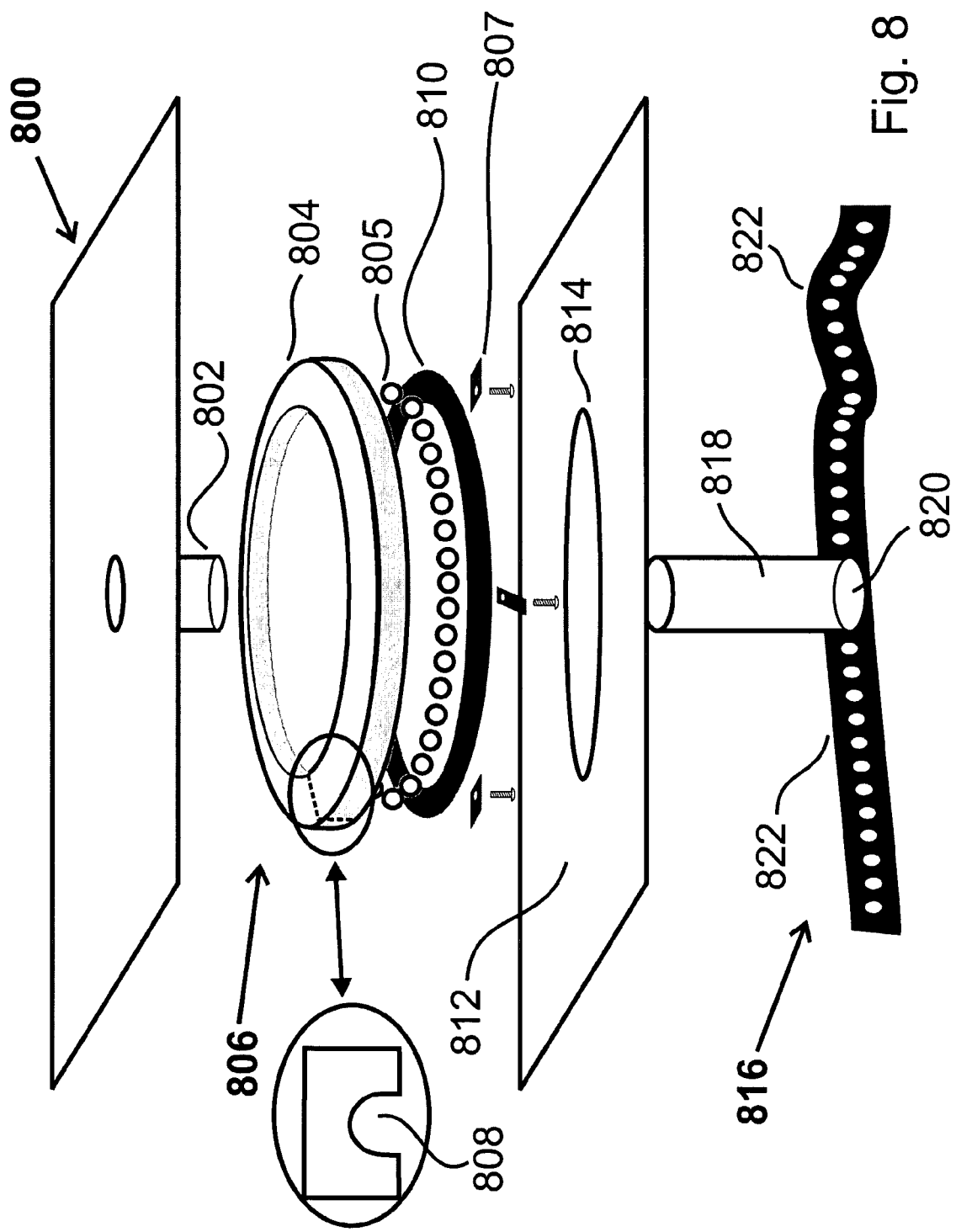
FIG. 8 shows an exploded, partial cutaway, partial perspective view of an embodiment of the present invention incorporating a "lazy susan" bearing.

The potential of entrapping the test subject may be further avoided by allowing the test subject to rotate within the confines of device 600, and the associated test equipment to rotate with the test subject, with respect to the rest of the portable device. Referring to FIG. 8, an exploded, partially cutaway, partially perspective view of the present invention incorporates a ball bearing assembly and bearing race, as manufactured by Bioanalytical Systems Inc., West Lafayette, Ind. Equipment support plate 800 comprises hollow pipe 802. Base 812 comprises hole 814. Harness holder 816 comprises sleeve 818, hole 820, and holes 822. Also shown is bearing 806 which comprises upper plate 804, ball bearings 805, hole 807, bearing race 808,lower plate 810 and support bracket 807. Upper plate 804 and lower plate 810 are in a fixed rotatable relationship with each other.

In use, equipment support plate 800 is fixedly attached to upper plate 804 of bearing 806 and lower plate 810 is fixedly attached to base 812. Hollow pipe 802 extends through hole 808 and beyond lower plate 810 and base 812, and acts as a conduit for various test leads operably connected to the test subject, including infusion catheters, wires, cables, blood sampling catheters and similar devices. Sleeve 818 protects the test leads from the test subject and is attached to hollow pipe 802. In this configuration, equipment may be placed on equipment support plate 800, and a test lead passed through hollow pipe 802, through hole 820 of harness holder 816, and connected to a test subject. The test subject is placed within, for example, a sling, which is then attached by straps or cord to harness holder 816 using holes 822.

Accordingly, when the test subject turns beneath base 812, torque is applied through the sling to harness holder 816. The torque is passed through sleeve 818, hollow pipe 802 and equipment plate 800 to upper plate 804 of bearing 806. Thus, upper plate 804, equipment plate 800 and harness holder 816 all rotate without kinking or placing stress on the tube connected to the test subject. Moreover, this allows the test subject to change direction even if base 812 is entrapped within a containment area, allowing the test subject to change course and extract himself along with portable device 600 and move out of the entrapment.

It will be appreciated by those skilled in the art that the above apparatus and method for monitoring and sampling is a significant improvement over the prior art. It permits the collection of blood samples, the continuous or intermittent infusion of a drug, the acquisition of heart rate and electrocardiograms, the collection of microdialysis or ultrafiltration samples, the acquisition of body temperature readings, and other data or samples that can be obtained by connection of a test lead or catheter between an animal and an external device. The use of such portable devices permits testing of larger animals, including but not limited to humans, pigs, cows, horses, dogs, sheep and goats while the animal is engaged in other activities. The device described in FIG. 1, when used with a human, would enable that human to utilize a private restroom facility without interrupting a test or monitoring session.

Additionally, the present invention eliminates test-related stress for an animal resulting from tethering or restriction, for the animal is not tethered and has freedom of movement. It is likely that the use of a mobile, automated blood sampling device would be less stressful for humans in a Phase 1 Clinical Trial, than repeated needle sticks over the course of a one or two day study that could demand as many as 24 blood samples from each test subject. It is anticipated that a portable automated blood sampling device, that could be wheeled over an incubator by medical personnel, could greatly alleviate the pain and emotional burden of repeated blood sticks from premature infants in neonatal intensive care wards by reducing the problem to a single insertion of an intravenous catheter. Thus, data retrieved by the present invention is free from artifacts that may be introduced due to induced stress. Moreover, the present invention allows for a number of additional devices to be easily incorporated into the device without significant reduction in the mobility of the test subject.

While the present invention has been described in detail with reference to certain exemplary embodiments thereof, such are offered by way of non-limiting examples of the invention, as other versions are possible. Moreover, a number of design choices exist within the scope of the present invention, some of which have been discussed above. It is anticipated that a variety of other modifications and changes will be apparent to those having ordinary skill in the art and that such modifications and changes are intended to be encompassed within the spirit and scope of the invention as defined by the following claims.

I claim:

1. A device for collecting blood samples from an animal, including:
   a syringe pump;
   a reservoir in fluid communication with the pump;
   a first valve that controls flow through a first conduit extending between the reservoir and an opening coupled to a catheter;
   a second valve that controls flow through a second conduit extending between the reservoir and a sample collection component; and
   a controller coupled to the pump and the valves and configured to cause collection of a blood sample by performing the steps of (i) actuating the pump to fill the reservoir and the conduits with a sterile fluid, (ii) opening the first valve and actuating the pump to draw blood from the catheter, through the first conduit and into the reservoir, thereby forming a blood/sterile fluid interface, (iii) opening the second valve and actuating the pump to force blood from the reservoir, through the second conduit and to the sample collection component, (iv) opening the first valve and actuating the pump to flush the first conduit with the sterile fluid, and (v) opening the second valve and actuating the pump to flush the second conduit with the sterile fluid;
   wherein the device is configured to be movable by the animal while the animal is physically connected to the device.

2. The device of claim 1, further including a third valve that controls flow through a third conduit having an inlet configured for connection to a supply of the sterile fluid, a first opening in fluid communication with the pump, and a second opening in fluid communication with the reservoir.

3. The device of claim 1, wherein the pump is a sterile syringe pump.

4. The device of claim 1, wherein the reservoir has a first tapered end coupled to the first and second conduits and a second tapered end in fluid communication with the pump.

5. The device of claim 1, wherein the sample collection component includes a first vial for collecting the blood during step (iii) and a second vial for collecting the sterile fluid during step (v).

6. The device of claim 1, wherein the controller is configured to perform the blood sample collection steps a plurality of times in succession.

7. The device of claim 6, wherein the sample collection component includes a plurality of sealed vials, the controller being configured to advance the plurality of sealed vials through a plurality of positions such that a different vial collects blood during step (iii) each time the blood sample collection steps are performed.

8. The device of claim 1, wherein the controller is configured to perform a series of preparation steps before performing the blood sample collection steps, the preparation steps including the steps of (i) actuating the pump to fill the pump with the sterile fluid, (ii) opening the second valve and actuating the pump to fill the reservoir and the second conduit with the sterile fluid, (iii) opening the first valve and actuating the pump to fill the first conduit with the sterile fluid before the catheter is coupled to the opening of the first conduit, (iii) opening the first valve and actuating the pump to draw a first amount of blood from the catheter after the catheter is coupled to the opening of the first conduit, and (iv) opening the second valve and actuating the pump to push blood through the second conduit, and (v) opening the first valve and actuating the pump to flush the reservoir with sterile fluid and to return blood in the reservoir and the first conduit through the catheter back to the animal.

9. The device of claim 1, further including a base for supporting at least a portion of the device, and a plurality of wheels connected to the base.

10. The device of claim 1, further including an alarm configured to indicate an interruption of power to the device.

11. A device for collecting blood samples from an animal, including:
    a closed fluid system, including
       a sterile pump being movable in a first direction to draw fluid into the pump and a second direction to expel fluid from the pump;
       a reservoir having a first opening and a second opening;
       a first conduit having a first opening configured for connection to a catheter to receive blood from the animal and a second opening in fluid communication with the first opening of the reservoir;
       a second conduit having a first opening configured for connection to a sample collection component and a second opening in fluid communication with the first opening of the reservoir;
       a third conduit having an inlet configured for connection to a supply of sterile fluid, a first opening in fluid communication with the pump, and a second opening in fluid communication with the second opening of the reservoir;
       a first valve operably connected to the first conduit, the first valve having an opened position that permits flow through the first conduit and a closed position that restricts flow through the first conduit;
       a second valve operably connected to the second conduit, the second valve having an opened position that permits flow through the second conduit and a closed position that restricts flow through the second conduit; and
       a third valve operably connected to the third conduit inlet, the third valve having an opened position that permits flow through the third conduit inlet and a closed position that restricts flow through the third conduit inlet; and
    a controller coupled to the fluid system for controlling the pump and the valves;

wherein the controller executes software to cause the fluid system to collect a blood sample from the animal, the software including instructions for performing the steps of
- (i) opening the first valve, and moving the pump in the first direction to draw blood through the first conduit and into the reservoir, thereby forming a blood / sterile fluid interface,
- (ii) opening the second valve, and moving the pump in the second direction to force blood from the reservoir, through the second conduit to the sample collection component,
- (iii) re-opening the first valve, and moving the pump in the second direction to force the sterile fluid out of the first opening of the first conduit, thereby flushing the first conduit,
- (iv) re-opening the second valve, and moving the pump in the second direction to force the sterile fluid out of the first opening of the second conduit, thereby flushing the second conduit and the sample collection component, and
- (v) opening the third valve, and moving the syringe in the first direction to draw the sterile fluid through the inlet of the third conduit and into the pump through the first opening of the third conduits wherein the device is configured to be movable by the animal while the animal is physically connected to the device.

12. The device of claim 11, wherein the sample collection component includes a first vial for collecting the blood during step (ii) and a second vial for collecting the sterile fluid during step (iv).

13. The device of claim 11, wherein the software further includes instructions for repeating steps (i)-(v) a plurality of times in succession.

14. The device of claim 13, wherein the sample collection component includes a plurality of sealed vials, the controller being configured to advance the plurality of sealed vials through a plurality of positions such that a different vial collects blood during step (ii) each time the blood sample collection steps are performed.

15. The device of claim 11, wherein the software further includes instructions for performing a series of preparation steps before performing the blood sample collection steps, the preparation steps including the steps of (i) actuating the pump to fill the pump with the sterile fluid, (ii) opening second valve, and actuating the pump to fill the reservoir and the second conduit with the sterile fluid, (iii) opening the first valve, and actuating the pump to fill the first conduit with the sterile fluid before the catheter is coupled to the opening of the first conduit, (iv) opening the first valve, and actuating the pump to draw a first amount of blood from the catheter after the catheter is coupled to the opening of the first conduit, and (v) opening the first valve, and actuating the pump to return the first amount of blood through the catheter to the animal.

16. The device of claim 11, further including a base for supporting the device, and a plurality of wheels connected to the base.

17. The device of claim 11, wherein the sample collection component includes a needle for depositing the blood and the sterile fluid into a plurality of vials.

18. The device of claim 11, further including a luer fitting coupled to the first opening of the first conduit and configured to connect to the catheter.

* * * * *